US012788690B2

(12) United States Patent
Denis et al.

(10) Patent No.: US 12,788,690 B2
(45) **Date of Patent: *Nov. 10, 2026**

(54) ANHYDROUS COMPOSITION FOR TOPICAL USE THAT IS IN THE FORM OF A DISPERSED PHASE BASED ON AT LEAST ONE SHORT DIOL IN A CONTINUOUS FATTY PHASE

(71) Applicant: SOCIETE D'EXPLOITATION DE PRODUITS POUR LES INDUSTRIES CHIMIQUES SEPPIC, Paris Cedex (FR)

(72) Inventors: Alice Denis, Castres (FR); Séverine Sigurani, Castres (FR); Catherine Bulcourt, La Garenne Colombes (FR)

(73) Assignee: SOCIETE D'EXPLOITATION DE PRODUITS POUR LES INDUSTRIES CHIMIQUES SEPPIC, Paris (FR)

( * ) Notice: Subject to any disclaimer, the term of this patent is extended or adjusted under 35 U.S.C. 154(b) by 1117 days.

This patent is subject to a terminal disclaimer.

(21) Appl. No.: 17/633,760

(22) PCT Filed: Aug. 4, 2020

(86) PCT No.: PCT/FR2020/051431

§ 371 (c)(1),
(2) Date: Feb. 8, 2022

(87) PCT Pub. No.: WO2021/028633

PCT Pub. Date: Feb. 18, 2021

(65) Prior Publication Data

US 2022/0378672 A1 Dec. 1, 2022

(30) Foreign Application Priority Data

Aug. 9, 2019 (FR) ....................................... 1909118

(51) Int. Cl.
*A61K 8/06* (2006.01)
*A61K 8/34* (2006.01)
(Continued)

(52) U.S. Cl.
CPC ................ *A61K 8/06* (2013.01); *A61K 8/345* (2013.01); *A61K 8/375* (2013.01); *A61K 8/604* (2013.01); *A61K 8/8188* (2013.01); *A61Q 5/02* (2013.01); *A61Q 19/001* (2013.01); *A61Q 19/04* (2013.01); *A61Q 19/10* (2013.01); *A61K 2800/31* (2013.01); *A61K 2800/5424* (2013.01); *A61K 2800/596* (2013.01)

(58) Field of Classification Search
CPC .......... A61K 8/06; A61K 8/345; A61K 8/375; A61K 8/604; A61K 8/8188; A61K 2800/31; A61K 2800/5424; A61K 2800/596; A61K 8/064; A61K 9/107; A61K 47/10; A61K 9/0014; A61K 8/86; A61K 8/8152; A61Q 5/02; A61Q 19/001; A61Q 19/04; A61Q 19/10; A61Q 19/00; A61Q 19/02; A61Q 5/00
See application file for complete search history.

(56) References Cited

U.S. PATENT DOCUMENTS 4,695,450 A * 9/1987 Bauer .................. A61K 9/4866
424/455
6,338,841 B1 1/2002 Mattai et al.
(Continued)

FOREIGN PATENT DOCUMENTS

CN 110101611 A * 8/2019 ............... A61K 8/06
DE 3938901 A1 * 5/1990 ............. C09K 23/00
(Continued)

OTHER PUBLICATIONS

CN110101611A—machine translation. Zeng et al. "Anhydrous vitamin A emulsion and preparation method thereof", 2019. (Year: 2019).*
Deckner et. al. SEPIGEL305 2013 (Year: 2013).*
Tadros "1 Emulsion Formation, Stability, and Rheology" Emulsion Formation and Stability, 2013, pp. 1-76. (Year: 2013).*
DE3938901A1—machine translation provided. Tully "Bestaendige Emulsion" DE3938901A1 1990 (Year: 1990).*
Tadros "Emulsion Formation and Stability", 2013. (Year: 2013).*
DE3938901A1—machine translation provided. Tully "Bestaendige Emulsion" 1990. (Year: 1990).*
Office Action, issued in Japanese Patent Application No. 2022-506694 dated Jul. 16, 2024.
(Continued)

*Primary Examiner* — Ali Soroush
*Assistant Examiner* — Rajan Pragani
(74) *Attorney, Agent, or Firm* — NIXON & VANDERHYE

(57) ABSTRACT

Composition for topical use including a gelled phase dispersed in a continuous phase, with: the gelled phase including a diol having 3-8 atoms and represented either by formula (Ia): $R^a1\text{-}C(R^b1)(OH)\text{—}C(OH)(R^c1)(R^d1)$ (Ia), in which each of the Ra1, Rb1, Rc1 and Rd1 radicals represent, independently of one another, a hydrogen atom or saturated aliphatic radical having 1-5 carbon atoms, or by formula (Ib): $R^a1\text{-}C(R^b1)(OH)\text{—}[C(R^e1)(R^f1)]t\text{-}C(OH)(R^c1)(R^d1)$ (Ib), in which t is equal to one, two or three, each of the $R^a1$, $R^b1$, $R^c1$, $R^d1$, $R^e1$ and $R^f1$ radicals represent, independently of one another, a hydrogen atom or saturated aliphatic radical having 1-5 carbon atoms, it being understood that at least one of the Ra1 or Rb1 radicals and/or at least one of the Rc1 or Rd1 radicals do not represent a hydrogen atom, and—a fatty phase including an oil, an emulsifying surfactant system and an emulsifying surfactant.

7 Claims, No Drawings

(51) Int. Cl.

| | |
|---|---|
| ***A61K 8/37*** | (2006.01) |
| ***A61K 8/60*** | (2006.01) |
| ***A61K 8/81*** | (2006.01) |
| ***A61Q 5/02*** | (2006.01) |
| ***A61Q 19/00*** | (2006.01) |
| ***A61Q 19/04*** | (2006.01) |
| ***A61Q 19/10*** | (2006.01) |

(56) References Cited

U.S. PATENT DOCUMENTS

| | | | | |
|---|---|---|---|---|
| 7,001,603 | B2 * | 2/2006 | Bagdi | A61Q 19/00 514/506 |
| 2002/0111281 | A1 * | 8/2002 | Vishnupad | A61Q 19/00 510/130 |
| 2002/0160023 | A1 | 10/2002 | Bagdi | |
| 2009/0208430 | A1 * | 8/2009 | Polonka | A61Q 19/04 424/59 |
| 2009/0292015 | A1 * | 11/2009 | Zhang | A61K 47/14 514/474 |
| 2011/0076245 | A1 * | 3/2011 | Braun | A61K 8/33 424/59 |
| 2014/0350101 | A1 * | 11/2014 | Arvidsson | A61K 9/0014 514/511 |
| 2016/0015609 | A1 * | 1/2016 | Merat | C08F 2/24 424/59 |
| 2018/0243188 | A1 | 8/2018 | Chan | |

FOREIGN PATENT DOCUMENTS

| | | | | |
|---|---|---|---|---|
| EP | 0 971 683 | A1 | 1/2000 | |
| EP | 1 459 801 | A2 | 9/2004 | |
| EP | 1 961 455 | A1 | 8/2008 | |
| FR | 3 004 454 | | 10/2014 | |
| JP | 2004519482 | A | 7/2004 | |
| JP | 2008239550 | A | 10/2008 | |
| JP | 2009280578 | A * | 12/2009 | A61K 8/064 |
| JP | 2016518486 | A | 6/2016 | |
| KR | 20150140366 | A * | 12/2015 | C08F 220/54 |
| WO | 96/00719 | A1 | 1/1996 | |
| WO | 98/44902 | A1 | 10/1998 | |
| WO | 02069889 | | 9/2002 | |
| WO | 02100374 | | 12/2002 | |
| WO | WO-2007066309 | A2 * | 6/2007 | A61K 8/375 |
| WO | 2009/156691 | | 12/2009 | |
| WO | 2014/167200 | A1 | 10/2014 | |
| WO | WO-2017062029 | A1 * | 4/2017 | A61P 17/00 |
| WO | 2017/180567 | | 10/2017 | |

OTHER PUBLICATIONS

International Search Report for PCT/FR2020/051431 mailed, Dated: 2021.

Written Opinion of the ISA for PCT/FR2020/051431, mailed Oct. 5, 2020, 8 pages.

Search Report for FR1909118, dated Apr. 20, 2020, 8 pages.

Vasiljevic et al., "An investigation into the characteristics and drug release properties of multiple W/O/W emulsion systems containing low concentration of lipophilic polymeric emulsifier", International Journal Of Pharmaceutics, vol. 309, No. 1-2, Feb. 17, 2006, pp. 171-177.

Office Action, issued in Japanese Patent Application No. 2022-506694 dated Jan. 28, 2025.

Office Action, issued in Korean Patent Application No. 10-2022-7007332 dated Jun. 9, 2025.

* cited by examiner

ANHYDROUS COMPOSITION FOR TOPICAL USE THAT IS IN THE FORM OF A DISPERSED PHASE BASED ON AT LEAST ONE SHORT DIOL IN A CONTINUOUS FATTY PHASE

This application is the U.S. national phase of International Application No. PCT/FR2020/051431 filed 4 Aug. 2020, which designated the U.S. and claims priority to FR Patent Application No. 1909118 filed 9 Aug. 2019, the entire contents of each of which are hereby incorporated by reference.

BACKGROUND OF THE INVENTION

Field of the Invention

The subject of the present invention is novel compositions in the form of a dispersion of a gelled phase, comprising at least one diol consisting of three to eight carbon atoms, in an oily phase, and also the uses thereof in cosmetics, in pharmaceuticals, in the textile industry, and in the paper industry.

Description of the Related Art

Cosmetic, dermocosmetic, dermopharmaceutical and pharmaceutical compositions can be in the form of aqueous solutions, of emulsions and of powders.

An emulsion is an initially heterogeneous mixture of two liquid substances which are immiscible with one another, the two substances being called "phases". Said mixture becomes macroscopically homogeneous through an external operation such as, for example, mechanical stirring with a suitable speed and mobile, or the addition of an amphiphilic substance called a surfactant. When presented in macroscopically homogeneous form, the mixture consists of a discontinuous phase, dispersed in the other phase which is called "continuous phase".

Emulsions are particularly preferred forms since they make it possible to convey both the water-soluble substances and liposoluble substances that are frequently used in these applications. A distinction is made between oil-in-water (O/W) emulsions in which the continuous phase consists of a hydrophilic phase, generally an aqueous phase, and the dispersed phase consists of a lipophilic fatty phase, and water-in-oil (W/O) emulsions in which the continuous phase consists of a lipophilic fatty phase and the dispersed phase consists of a hydrophilic phase, generally an aqueous phase.

Oil-in-water emulsions are intrinsically more stable than water-in-oil emulsions; water-in-oil emulsions nevertheless have a number of advantages. Specifically, the separation between the water droplets reduces the possibility of the proliferation of microorganisms. Furthermore, the use of preserving agents, which is essential when the continuous phase is aqueous, can be avoided or reduced when the continuous phase is fatty. Water-in-oil emulsions are far less sensitive to low temperature than oil-in-water emulsions. Lastly, for topical applications for cosmetic use, the European patent application published under the number EP 1961455 A1 discloses that an oily continuous phase makes it possible to cover the skin after application of the water-in-oil emulsion, which protects the skin from dehydration and against external substances by forming a persistent oily film, thus making it possible to treat dry skin.

The solutions proposed in the prior art for preparing dermatological emulsions which are in the water-in-oil form are not satisfactory because either the silicone derivatives employed are volatile and may have harmful effects with regard to the environment and the users, or the silicone derivatives employed are not very volatile and then they impart unpleasant sensorial properties after topical application, such as for example sticky sensations on the skin.

The European patent application published under the number EP 1 459 801 A2 and the international patent application published under the number WO 2014/167200A1 disclose the preparation of water-in-oil emulsions comprising, per 100% of their weights, from 60% to 98% by weight of aqueous phase gelled by virtue of the presence therein of a crosslinked polyelectrolyte, making it possible to partially solve the technical problem. In fact, the water-in-oil emulsions obtained are characterized by better persistence when applied to the skin, making it possible to withstand sweat, bathing water or rain water. However, in a persistent improvement approach, research is directed toward the preparation of galenic forms even more resistant to water and to sweat, also making it possible to convey several cosmetic or pharmaceutical active ingredients which are either partially insoluble or unstable in an aqueous medium.

SUMMARY OF THE INVENTION

This is why the inventors have sought to develop new emulsions in which the continuous phase is oily and the dispersed phase is polar but non-aqueous, free of added water, which do not exhibit the drawbacks described above, and which remain homogeneous at ambient temperature (greater than or equal to 20° C. and less than or equal to 25° C.) and at 45° C. after storage for at least three months.

A solution of the present invention is a composition (E1) for topical use comprising a gelled phase (A1) free of added water and dispersed in a continuous phase (A2), with:

- the gelled phase (A1) comprising at least one diol chosen from 1,2-propanediol, 1,2-butanediol, 1,3-butanediol, 1,2-pentanediol, 1,2-hexanediol, 1,2-octanediol, 2,3-butanediol, 2,3-pentanediol, 2,3-hexanediol, 2,5-hexanediol or 2-methyl 2,4-pentanediol, and
- a fatty phase (A2) comprising at least one oil, at least one emulsifying surfactant (S1) and at least one emulsifying surfactant (S2).

Preferably, said composition (E1) comprises, per 100% of its weight:

- from 60% to 98% by weight, preferably from 60% to 95% by weight, and even more preferentially from 60% to 90% by weight of the gelled phase (A1), and
- from 2% to 40% by weight, preferably from 5% to 40% by weight, and even more preferentially from 10% to 40% by weight of the fatty phase (A2).

The emulsifying surfactant (S1) is preferably selected from the elements of the group consisting of alkylpolyglycoside compositions and compositions of alkylpolyglycosides and of fatty alcohols, and the emulsifying surfactant (S2) is preferably selected from the elements of the group consisting of polyglycerol esters, alkoxylated polyglycerol esters, polyglycol polyhydroxystearates, polyglycerol polyhydroxystearates and alkoxylated polyglycerol polyhydroxystearates.

The expression "for topical use" used in the definition of the composition (E1) according to the invention, which is in the form of a dispersion of a gelled phase (A1) in a continuous phase (A2) and as defined above, means that said composition (E1) is employed by application to the skin, the hair, the scalp or the lips, whether it is a direct application in the case of a cosmetic, dermocosmetic, dermopharmaceutical or pharmaceutical composition or an indirect application, for example in the case of a body hygiene product in the form of a textile or paper wipe or of health products intended to be in contact with the skin or the lips.

For the purposes of the present invention, the term "gelled phase (A1)" denotes a homogeneous phase characterized in that the dynamic viscosity of said phase (A1), measured at a temperature of 20° C. and using a Brookfield LVT viscometer at a speed of 6 revolutions/minute, is greater than or equal to 1000 mPa·s and less than or equal to 100 000 mPa·s, more particularly greater than or equal to 10 000 mPa·s and less than or equal to 100 000 mPa·s.

Depending on the case, the composition according to the invention can exhibit one or more of the following characteristics:

- the gelled phase (A1) comprises, per 100% of its weight, from 0.5% to 10% by weight of a crosslinked anionic polyelectrolyte (AP1), and from 90% to 99.5% by weight of at least one diol chosen from 1,2-propanediol, 1,2-butanediol, 1,3-butanediol, 1,2-pentanediol, 1,2-hexanediol, 1,2-octanediol, 2,3-butanediol, 2,3-pentanediol, 2,3-hexanediol, 2,5-hexanediol or 2-methyl-2,4-pentanediol. It should be noted that, preferably, the gelled phase (A1) comprises per 100% of its weight, from 0.5% to 8.5% by weight, more particularly from 0.5% to 7% by weight of a crosslinked anionic polyelectrolyte (AP1) and from 91.5% to 99.5% by weight, more particularly from 93% to 99.5% by weight of at least one diol chosen from 1,2-propanediol, 1,2-butanediol, 1,3-butanediol, 1,2-pentanediol, 1,2-hexanediol, 1,2-octanediol, 2,3-butanediol, 2,3-pentanediol, 2,3-hexanediol, 2,5-hexanediol or 2-methyl-2,4-pentanediol;
- said diol is chosen from 1,2-propanediol, 1,2-butanediol, 1,3-butanediol, 1,2-pentanediol, 1,2-hexanediol or 2-methyl-2,4-pentanediol;
- the crosslinked anionic polyelectrolyte (AP1) comprises a proportion of greater than or equal to 25 mol % of monomer units derived from 2-methyl-2-[(1-oxo-2-propenyl)amino]-1-propanesulfonic acid in free acid or partially or totally salified form;
- the emulsifying surfactant ($S_1$) consists of at least one alkylpolyglycoside composition ($C_1$) represented by formula (VII):

$$R_1—O—(G)x—H \quad \text{(VII)}$$

wherein x represents a decimal number between 1.05 and 2.5, G represents the glucosyl or α,β-D-glucopyranosyl radical, obtained from the removal of the hemiacetal hydroxyl group from α,β-D-glucopyranose, and $R_1$ represents a radical chosen from the elements of the group consisting of the radicals n-dodecyl, n-tetradecyl, n-hexadecyl, n-octadecyl, n-eicosyl and n-behenyl, said composition ($C_1$) consisting of a mixture of compounds represented by formulae ($VII_1$), ($VII_2$), ($VII_3$), ($VII_4$) and ($VII_5$):

$$R_1—O—(G)_1—H \quad (VII_1)$$

$$R_1—O—(G)_2—H \quad (VII_2)$$

$$R_1—O—(G)_3—H \quad (VII_3)$$

-continued $$R_1—O—(G)_4—H \quad (VII_4)$$

$$R_1—O—(G)_5—H \quad (VII_5)$$

in the respective molar proportions $a_1$, $a_2$, $a_3$, $a_4$ and $a_5$, such that the sum $a_1+a_2+a_3+a_4+a_5$ is equal to 1 and that the sum $a_1+2a_2+3a_3+4a_4+5a_5$ is equal to x;

- the emulsifying surfactant ($S_1$) consists of at least one composition ($C_2$) comprising, per 100% of its weight:
  - from 10% to 50% by weight of at least one alkylpolyglycoside composition ($C_1$) represented by formula (VII):

$$R_1—O—(G)x—H, \quad \text{(VII)}$$

wherein x represents a decimal number between 1.05 and 2.5, G represents the glucosyl or α,β-D-glucopyranosyl radical, obtained from the removal of the hemiacetal hydroxyl group from α,β-D-glucopyranose, and $R_1$ represents a radical chosen from the elements of the group consisting of the radicals n-dodecyl, n-tetradecyl, n-hexadecyl, n-octadecyl, n-eicosyl and n-behenyl, said composition consisting of a mixture of compounds represented by formulae ($VII_1$), ($VII_2$), ($VII_3$), ($VII_4$) and ($VII_5$):

$$R1—O—(G)1—H \quad \text{(VII1)}$$

$$R1—O—(G)2—H \quad \text{(VII2)}$$

$$R1—O—(G)3—H \quad \text{(VII3)}$$

$$R1—O—(G)4—H \quad \text{(VII4)}$$

$$R1—O—(G)5—H \quad \text{(VII5)}$$

in the respective molar proportions $a_1$, $a_2$, $a_3$, $a_4$ and $a_5$, such that the sum $a_1+a_2+a_3+a_4+a_5$ is equal to 1 and that the sum $a_1+2a_2+3a_3+4a_4+5a_5$ is equal to x; and

- from 90% to 50% by weight of at least one fatty alcohol of formula (VIII):

$$R''_1—OH, \quad \text{(VIII)}$$

wherein $R''_1$ represents a radical chosen from the elements of the group consisting of the radicals n-dodecyl, n-tetradecyl, n-hexadecyl, n-octadecyl, n-eicosyl and n-behenyl, where $R''_1$ may be identical to or different from $R_1$;

- the emulsifying surfactant ($S_1$) consists of at least one alkylpolyglycoside composition ($C'_1$) represented by formula (IX):

$$R_1—O—(G)_x—H \quad \text{(IX)}$$

wherein x represents a decimal number between 1.05 and 2.5, G represents the xylose residue and $R_1$ represents the 2-octyldodecyl radical, said composition ($C'_1$) consisting of a mixture of compounds represented by the formulae ($IX_1$), ($IX_2$), ($IX_3$), ($IX_4$) and ($IX_5$):

$$R_1—O—(G)_1—H \quad (IX_1)$$

$$R_1—O—(G)_2—H \quad (IX_2)$$

$$R_1—O—(G)_3—H \quad (IX_3)$$

$$R_1—O—(G)_4—H \quad (IX_4)$$

$$R_1—O—(G)_5—H \quad (IX_5)$$

in the respective molar proportions $a_1$, $a_2$, $a_3$, $a_4$ and $a_5$, such that the sum $a_1+a_2+a_3+a_4+a_5$ is equal to 1 and that the sum $a_1+2a_2+3a_3+4a_4+5a_5$ is equal to x;

said emulsifying system (S) consists of a composition ($C'_2$) comprising, per 100% of its weight:

from 10% to 50% by weight of at least one alkylpolyglycoside composition (C'1) represented by formula (X):

$$R_1—O—(G)_x—H \quad (X)$$

wherein x represents a decimal number between 1.05 and 2.5, G represents the xylose residue and $R_1$ represents the 2-octyldodecyl radical, said composition consisting of a mixture of compounds represented by formulae ($X_1$), ($X_2$), ($X_3$), ($X_4$) and ($X_5$):

$$R_1—O—(G)_1—H \quad (X_1)$$

$$R_1—O—(G)_2—H \quad (X_2)$$

$$R_1—O—(G)_3—H \quad (X_3)$$

$$R_1—O—(G)_4—H \quad (X_4)$$

$$R_1—O—(G)_5—H \quad (X_5)$$

in the respective molar proportions $a_1$, $a_2$, $a_3$, $a_4$ and $a_5$, such that the sum $a_1+a_2+a_3+a_4+a_5$ is equal to 1 and that the sum $a_1+2a_2+3a_3+4a_4+5a_5$ is equal to x; and from 90% to 50% by weight of at least one fatty alcohol of formula (XI):

$$R'''_1—OH, \quad (XI)$$

wherein $R'''_1$ represents the 2-octyldodecyl radical;

the emulsifying surfactant ($S_2$) consists of at least one polyglycol polyhydroxystearate represented by formula (XII):

[Chem 1]

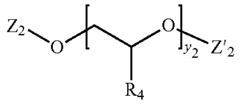

(XII)

wherein y2 represents an integer greater than or equal to 2 and less than or equal to 50, $R_4$ represents a hydrogen atom, a methyl radical or an ethyl radical, and $Z_2$ represents a radical of formula (XIII):

[Chem 2]

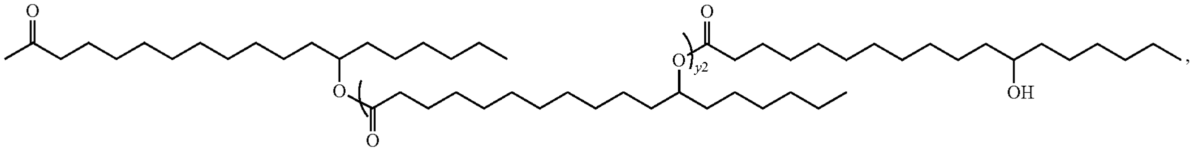

(XIII)

wherein $y'_2$ represents an integer greater than or equal to 0 and less than or equal to 10, more particularly greater than or equal to 1 and less than or equal to 10, and $Z'_2$ represents a radical of formula (XIII) as defined above, where $Z'_2$ may be identical to or different from $Z_2$, or a hydrogen atom;

said composition (E1) for topical use comprises one or more auxiliary compounds chosen from foaming and/or detergent surfactants, thickening and/or gelling surfactants, thickening and/or gelling agents, stabilizers, film-forming compounds, solvents and cosolvents, hydrotropic agents, plasticizers, emulsifiers and co-emulsifiers, opacifiers, self-tanning agents, nacreous agents, superfatting agents, sequestrants, chelating agents, antioxidants, fragrances, essential oils, preserving agents, conditioning agents, deodorants, bleaching agents intended for bleaching bodily hair and the skin, active ingredients intended to provide a treating and/or protective action to the skin or the hair, sunscreens, mineral fillers or pigments, particles that give a visual effect or that are intended for encapsulating active agents, exfoliant particles, texturing agents, optical brighteners and insect repellents. In general, the composition (E1) for topical use according to the invention can comprise excipients and/or active ingredients commonly used in the field of formulations for topical use, in particular cosmetic, dermocosmetic, pharmaceutical or dermopharmaceutical use;

said composition comprises, per 100% of its weight, a proportion of between 0.5% by weight and 10% by weight of one or more self-tanning agents. Preferably, said self-tanning agent will be chosen from the elements of the group consisting of dihydroxyacetone, erythrulose, glyceraldehyde, isatin, alloxan, ninhydrin, and mesotartaric aldehyde, and preferably from dihydroxyacetone and erythrulose. Thus, said composition comprising the self-tanning agent will preferably be used for artificially tanning and/or browning human skin and a subject of the present invention will also be a cosmetic treatment process for artificially tanning and/or browning human skin, comprising at least one step of applying the above composition (E1) to said human skin.

A subject of the present invention is also the use of the composition ($E_1$) as defined above, for the cosmetic treatment of the skin, the hair, the scalp and/or lips.

Preferably, said composition (E1) will be a composition for cleansing, protecting or caring for the skin, the hair, the scalp or the lips.

Preferably, the fatty phase (A2) comprises, per 100% of its weight:

- from 1.25% to 25% by weight, more particularly from 1.25% to 20% by weight, of an emulsifying system (S) comprising, per 100% by weight of said emulsifying system (S):
- from 12% to 88% by weight, more particularly from 15% to 85% by weight, and more particularly still from 20% by weight to 85% by weight, of at least one emulsifying surfactant (S1), and
- from 12% to 88% by weight, more particularly from 15% to 85% by weight, and more particularly still from 20% by weight to 85% by weight, of at least one emulsifying surfactant (S2);
- from 75% to 98.75% by weight, more particularly from 80% to 98.75% by weight, and more particularly still from 82% to 98.75% by weight, of at least one oil and optionally of at least one wax.

The term "oil" denotes a compound and/or a mixture of compounds that are water-insoluble, and liquid at 25° C., and more particularly:

- linear alkanes including from 11 to 19 carbon atoms;
- branched alkanes comprising from 7 to 40 carbon atoms, such as isododecane, isopentadecane, isohexadecane, isoheptadecane, isooctadecane, isononadecane or isoeicosane, or mixtures of some of them, such as those mentioned below and identified by their INCI name: $C_{7-8}$ isoparaffin, $C_{8-9}$ isoparaffin, $C_{9-11}$ isoparaffin, $C_{9-12}$ isoparaffin, $C_{9-13}$ isoparaffin, $C_{9-14}$ isoparaffin, $C_{9-16}$ isoparaffin, $C_{10-11}$ isoparaffin, $C_{10-12}$ isoparaffin, $C_{10-13}$ isoparaffin, $C_{11-12}$ isoparaffin, $C_{11-13}$ isoparaffin, $C_{11-14}$ isoparaffin, $C_{12-14}$ isoparaffin, $C_{12-20}$ isoparaffin, $C_{13-14}$ isoparaffin, $C_{13-16}$ isoparaffin;
- cycloalkanes optionally substituted with one or more linear or branched alkyl radicals;
- white mineral oils, such as the products sold under the following names: Marcol™ 52, Marcol™ 82, Drakeol™ 6VR, Eolane™ 130, Eolane™ 150;
- hemisqualane (or 2,6,10-trimethyldodecane; CAS number: 3891-98-3), squalane (or 2,6,10,15,19,23-hexamethyltetracosane), hydrogenated polyisobutene or hydrogenated polydecene;
- mixtures of alkanes including from 15 to 19 carbon atoms, said alkanes being linear alkanes, branched alkanes and cycloalkanes, and more particularly the mixture ($M_1$) which comprises, per 100% of its weight, a proportion by weight of branched alkanes of greater than or equal to 90% and less than or equal to 100%; a proportion by weight of linear alkanes of greater than or equal to 0% and less than or equal to 9%, and more particularly less than 5%, and a proportion by weight of cycloalkanes of greater than or equal to 0% and less than or equal to 1%, for example the mixtures sold under the name Emogreen™ L15 or Emogreen™ L19;

- the fatty alcohol ethers of formula (II):

$$Z_1—O—Z_2, \quad (II)$$

wherein $Z_1$ and $Z_2$, which may be identical or different, represent a linear or branched alkyl radical including from 5 to 18 carbon atoms, for example dioctyl ether, didecyl ether, didodecyl ether, dodecyl octyl ether, dihexadecyl ether, (1,3-dimethylbutyl) tetradecyl ether, (1,3-dimethylbutyl) hexadecyl ether, bis(1,3-dimethylbutyl) ether or dihexyl ether.

- the monoesters of fatty acids and of alcohols of formula (III):

$$R'_1—(C{=}O)—O—R'_2, \quad (III)$$

wherein $R'_1$—(C═O) represents a saturated or unsaturated, linear or branched acyl radical comprising from 8 to 24 carbon atoms, and R'2 represents, independently of $R'_1$, a saturated or unsaturated, linear or branched hydrocarbon-based chain comprising from 1 to 24 carbon atoms, for example methyl laurate, ethyl laurate, propyl laurate, isopropyl laurate, butyl laurate, 2-butyl laurate, hexyl laurate, methyl cocoate, ethyl cocoate, propyl cocoate, isopropyl cocoate, butyl cocoate, 2-butyl cocoate, hexyl cocoate, methyl myristate, ethyl myristate, propyl myristate, isopropyl myristate, butyl myristate, 2-butyl myristate, hexyl myristate, octyl myristate, methyl palmitate, ethyl palmitate, propyl palmitate, isopropyl palmitate, butyl palmitate, 2-butyl palmitate, hexyl palmitate, octyl palmitate, methyl oleate, ethyl oleate, propyl oleate, isopropyl oleate, butyl oleate, 2-butyl oleate, hexyl oleate, octyl oleate, methyl stearate, ethyl stearate, propyl stearate, isopropyl stearate, butyl stearate, 2-butyl stearate, hexyl stearate, octyl stearate, methyl isostearate, ethyl isostearate, propyl isostearate, isopropyl isostearate, butyl isostearate, 2-butyl isostearate, hexyl isostearate, isostearyl isostearate;

- diesters of fatty acids and of glycerol of formula (IV) and of formula (V):

$$R'_3—(C{=}O)—O—CH_2—CH(OH)—CH_2—O—(C{=}O)—R'_4 \quad (IV)$$

$$R'_5—(C{=}O)—O—CH_2—CH[O—(C{=}O)—R'_6]—CH_2—OH, \quad (V)$$

formulae (IV) and (V) wherein $R'_3$—(C═O), $R'_4$—(C═O), $R'_5$—(C═O) and $R'_6$—(C═O), which may be identical or different, represent a saturated or unsaturated, linear or branched acyl group including from 8 to 24 carbon atoms;

- triesters of fatty acids and of glycerol of formula (VI):

$$R'_7—(C{=}O)—O—CH_2\,CH[O—(C{=}O)—R''_8]—CH_2{\cdot}O—(C{=}O)—R''_9, \quad (VI)$$

wherein $R'_7$—(C═O), $R'_8$—(C═O) and $R'_9$—(C═O), which may be identical or different, represent a saturated or unsaturated, linear or branched acyl group including from 8 to 24 carbon atoms.

- plant oils, such as phytosqualane, sweet almond oil, coconut kernel oil, castor oil, jojoba oil, olive oil, rapeseed oil, groundnut oil, sunflower oil, wheat germ oil, corn germ oil, soybean oil, cottonseed oil, alfalfa oil, poppy seed oil, pumpkin seed oil, evening primrose oil, millet oil, barley oil, rye oil, safflower oil, candlenut oil, passionflower oil, hazelnut oil, palm oil, shea butter, apricot kernel oil, beauty-leaf oil, sisymbrium oil, avocado oil, calendula oil, oils derived from flowers or vegetables;

ethoxylated plant oils.

Preferably, the composition according to the invention comprises at least one oil chosen from the elements of the group consisting of castor oil, liquid paraffins, cocoyl caprylate/caprate, isopropyl myristate and capric/caprylic triglyceride.

The fatty phase (A2) optionally comprises wax. The latter is more particularly chosen from beeswax, carnauba wax, candelilla wax, ouricury wax, Japan wax, cork fiber wax, sugarcane wax, paraffin waxes, lignite waxes, microcrystalline waxes, lanolin wax; ozokerite; polyethylene wax; silicone waxes; plant waxes; fatty alcohols and fatty acids that are solid at ambient temperature; glycerides that are solid at ambient temperature.

In the definition of composition (E1) for topical use that is a subject of the present invention, the term "crosslinked anionic polyelectrolyte (AP1)" denotes a non-linear crosslinked anionic polyelectrolyte, which is in the form of a three-dimensional network which is insoluble in water but swellable in water and which leads to the production of a chemical gel.

Preferably, the crosslinked anionic polyelectrolyte (AP1) comprises, per 100 mol %:

(a1)—a proportion of greater than or equal to 25 mol % and less than or equal to 100 mol % of monomer units derived from 2-methyl-2-[(1-oxo-2-propenyl)amino]-1-propanesulfonic acid in free acid or partially or totally salified form;

(a2)—optionally, a proportion of greater than 0 mol % and less than or equal to 75 mol % of monomer units derived from at least one monomer chosen from the elements of the group consisting of acrylamide, N,N-dimethylacrylamide; methacrylamide or N-isopropylacrylamide;

(a3)—optionally, a proportion of greater than 0 mol % and less than or equal to 20 mol %, more particularly greater than 0 mol % and less than or equal to 15 mol %, more particularly still greater than or equal to 0 mol % and less than or equal to 10 mol % of monomer units derived from at least one monomer chosen from the elements of the group consisting of (2-hydroxyethyl) acrylate, (2,3-dihydroxypropyl) acrylate, (2-hydroxyethyl) methacrylate, (2,3-dihydroxypropyl) methacrylate and vinylpyrrolidone;

(a4)—optionally, a proportion of greater than 0 mol % and less than or equal to 75 mol % of monomer units derived from at least one monomer chosen from the elements of the group consisting of acrylic acid, methacrylic acid, 2-carboxyethylacrylic acid, itaconic acid, maleic acid and 3-methyl-3-[(1-oxo-2-propenyl) amino]butanoic acid, the carboxylic function of said monomers being in free acid, partially salified or totally salified form;

(a5)—optionally, a proportion of greater than 0 mol % and less than or equal to 5 mol % of at least one monomer of formula (M1):

[Chem 3]

(M1)

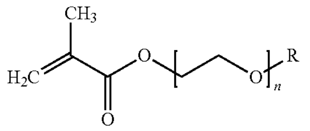

wherein R represents a linear or branched alkyl radical comprising from eight to twenty carbon atoms and n represents an integer of greater than or equal to zero and of less than or equal to twenty;

(a6)—a proportion of greater than 0 mol % and of less than or equal to 1 mol % of monomer units resulting from at least one diethylenic or polyethylenic crosslinking monomer (AR); the sum of said molar proportions as monomer units according to a1), a2), a3), a4), a5) and a6) being equal to 100 mol %.

For the purposes of the present invention, the term "salified" means that the acid function present in a monomer is in an anionic form associated in salt form with a cation, notably alkali metal salts, such as the sodium or potassium cations, or such as cations of nitrogenous bases such as the ammonium salt, the lysine salt or the monoethanolamine salt ($HOCH_2$—$CH_2$—$NH_4^+$). They are preferably sodium or ammonium salts.

At least one diethylenic or polyethylenic crosslinking monomer (AR) in particular denotes, in the definition of said crosslinked anionic polyelectrolyte (AP1), a monomer chosen from the elements of the group consisting of methylenebis(acrylamide), ethylene glycol dimethacrylate, diethylene glycol diacrylate, ethylene glycol diacrylate, diallylurea, triallylamine, trimethylolpropane triacrylate, diallyloxyacetic acid or one of its salts, such as sodium diallyloxyacetate, or a mixture of these compounds; and more particularly a monomer chosen from ethylene glycol dimethacrylate, triallylamine, trimethylolpropane triacrylate or methylenebis(acrylamide) or a mixture of these compounds.

According to another particular aspect of the present invention, the composition ($E_1$) for topical use is characterized in that said crosslinking monomer (AR) as defined above is used in a molar proportion of less than or equal to 0.5%, more particularly less than or equal to 0.25% and most particularly less than or equal to 0.1%; it is more particularly greater than or equal to 0.005 mol %.

The crosslinked anionic polyelectrolyte (AP1) used in the composition ($E_1$) for topical use which is a subject of the present invention may also comprise various additives such as complexing agents, transfer agents or chain-limiting agents.

The crosslinked anionic polyelectrolyte (AP1) used in the composition ($E_1$) for topical use which is a subject of the present invention may be prepared by performing a radical polymerization process known to those skilled in the art, for instance processes of solution polymerization, suspension polymerization, inverse suspension polymerization, emulsion polymerization, inverse emulsion polymerization or polymerization in solvent medium followed by a step of precipitation of the polymer formed.

According to a more particular aspect, the crosslinked anionic polyelectrolyte (AP1) used in the composition ($E_1$) for topical use which is a subject of the present invention may be prepared by performing a process of polymerization in solvent medium followed by a step of precipitation of the polymer formed, or of inverse emulsion polymerization optionally followed by a step of concentration and/or atomization.

According to a more particular aspect, the crosslinked anionic polyelectrolyte (AP1) used in the composition ($E_1$) for topical use which is a subject of the present invention may be prepared according to one of the processes described above and may involve the use of transfer agents or chain-limiting agents. The transfer agents or chain-limiting agents are more particularly chosen from the group consisting of sodium hypophosphite, alcohols of low molecular weight, for example methanol, ethanol, 1-propanol, isopropanol or butanol, thiols, for example 2-mercaptoethanol, transfer agents comprising a sulfate function, for example sodium methallylsulfonate, or mixtures of said transfer agents. The transfer or chain-limiting agents are more particularly used in molar proportions, expressed with respect to the total number of moles of monomers employed, of 0.001 mol % to 1 mol %, more particularly of 0.001 mol % to 0.5 mol % and very particularly of 0.001 mol % to 0.1 mol %.

According to another particular aspect of the present invention, said crosslinked anionic polyelectrolyte (AP1) is an element of the group consisting of a homopolymer of 2-methyl-2-[(1-oxo-2-propenyl)amino]-1-propanesulfonic acid partially or totally salified in sodium salt or ammonium salt form, crosslinked with triallylamine and/or methylenebis(acrylamide); a copolymer of 2-methyl-2-[(1-oxo-2-propenyl)amino]-1-propanesulfonic acid partially or totally salified in sodium salt or ammonium salt form and of acrylic acid partially or totally salified in sodium salt or ammonium salt form, crosslinked with triallylamine and/or methylenebis(acrylamide); a copolymer of 2-methyl-2-[(1-oxo-2-propenyl)amino]-1-propanesulfonic acid (γ) partially or totally salified in sodium salt or ammonium salt form and of acrylic acid (δ) partially or totally salified in sodium salt form in a molar ratio (γ)/(δ) of greater than or equal to 30/70 and less than or equal to 90/10, crosslinked with triallylamine and/or methylenebis(acrylamide); a copolymer of 2-methyl-2-[(1-oxo-2-propenyl)amino]-1-propanesulfonic acid (γ) partially or totally salified in sodium salt form, and of acrylic acid (δ) partially or totally salified in sodium salt form in a molar ratio (γ)/(δ) of greater than or equal to 40/60 and less than or equal to 90/10, crosslinked with triallylamine and/or methylenebis(acrylamide); a copolymer of 2-methyl-2-[(1-oxo-2-propenyl)amino]-1-propanesulfonic acid (γ) partially or totally salified in sodium salt form, and of acrylamide (ε) in a molar ratio (γ)/(ε) of greater than or equal to 30/70 and less than or equal to 90/10, crosslinked with triallylamine and/or methylenebis(acrylamide); a copolymer of 2-methyl-2-[(1-oxo-2-propenyl)amino]-1-propanesulfonic acid (γ) partially or totally salified in sodium salt form, and of hydroxyethyl acrylate (ζ) in a molar ratio (γ)/(ζ) of greater than or equal to 30/70 and less than or equal to 90/10, crosslinked with triallylamine and/or methylenebis(acrylamide); a terpolymer crosslinked with triallylamine and/or methylenebis(acrylamide), of 2-methyl-2-[(1-oxo-2-propenyl)amino]-1-propanesulfonic acid partially or totally salified in sodium salt or ammonium salt form, of acrylamide and of acrylic acid partially or totally salified in sodium salt or ammonium salt form; a terpolymer crosslinked with triallylamine and/or methylenebis(acrylamide), of 2-methyl-2-[(1-oxo-2-propenyl)amino]-1-propanesulfonic acid partially or totally salified in sodium salt or ammonium salt form in a molar proportion of greater than or equal to 30% and less than or equal to 45%, of acrylamide in a molar proportion of greater than or equal to 45% and less than or equal to 68% and of acrylic acid partially or totally salified in sodium salt or ammonium salt form in a molar proportion of greater than or equal to 2% and less than or equal to 10%; a terpolymer crosslinked with triallylamine and/or methylenebis(acrylamide), of 2-methyl-2-[(1-oxo-2-propenyl)amino]-1-propanesulfonic acid partially or totally salified in sodium salt or ammonium salt form in a molar proportion of greater than or equal to 30% and less than or equal to 45%, of acrylamide in a molar proportion of greater than or equal to 47% and less than or equal to 68% and of acrylic acid partially or totally salified in sodium salt or ammonium salt form in a molar proportion of greater than or equal to 2% and less than or equal to 8%; a terpolymer crosslinked with trimethylolpropane triacrylate and/or triallylamine and/or methylenebis(acrylamide), of 2-methyl-2-[(1-oxo-2-propenyl)amino]-1-propanesulfonic acid partially or totally salified in sodium salt or ammonium salt form in a molar proportion of greater than or equal to 60% and less than or equal to 80%, of N,N-dimethylacrylamide in a molar proportion of greater than or equal to 15% and less than or equal to 39.5% and of tetraethoxylated lauryl methacrylate in a molar proportion of greater than or equal to 0.5% and less than or equal to 5%; a tetrapolymer crosslinked with trimethylolpropane triacrylate and/or triallylamine and/or methylenebis(acrylamide), of 2-methyl-2-[(1-oxo-2-propenyl)amino]-1-propanesulfonic acid partially or totally salified in sodium salt or ammonium salt form in a molar proportion of greater than or equal to 60% and less than or equal to 80%, of N,N-dimethylacrylamide in a molar proportion of greater than or equal to 15% and less than or equal to 39%, of lauroyl methacrylate in a molar proportion of greater than or equal to 0.5% and less than or equal to 2.5%, and of stearoyl methacrylate in a molar proportion of greater than or equal to 0.5% and less than or equal to 2.5%.

Regarding the emulsifying surfactant, in formula (VII) as defined above, the group R1-O— is linked to G via the anomeric carbon of the saccharide residue, so as to form an acetal function.

According to one particular aspect, in the definition of formula (VII) x, or mean degree of polymerization, represents a decimal number greater than or equal to 1.05 and less than or equal to 2.5, more particularly greater than or equal to 1.05 and less than or equal to 2.0 and more particularly still greater than or equal to 1.25 and less than or equal to 2.0.

According to another particular aspect, the combination of at least one emulsifying surfactant (S1) and at least one emulsifying surfactant (S2) comprises, per 100% of its weight:

- from 12% to 88% by weight of at least one emulsifying surfactant ($S_1$) which consists of at least one composition ($C_2$) comprising, per 100% of its weight:
  - from 10% to 50% by weight of at least one alkylpolyglycoside composition ($C_1$) represented by formula (VII):

$$R_1—O—(G)_x—H \qquad \text{(VII)}$$

wherein x represents a decimal number between 1.05 and 2.5, G represents the glucosyl or α,β-D-glucopyranosyl radical, obtained from the removal of the hemiacetal hydroxyl group from α,β-D-glucopyranose, and $R_1$ represents a radical chosen from the elements of the group consisting of the radicals n-dodecyl, n-tetradecyl, n-hexadecyl, n-octadecyl, n-eicosyl and n-behenyl, said composition consisting of a mixture of compounds represented by formulae ($VII_1$), ($VII_2$), ($VII_3$), ($VII_4$) and ($VII_5$):

$$R_1—O—(G)_1—H \quad (VII_1)$$

$$R_1—O—(G)_2—H \quad (VII_2)$$

$$R_1—O—(G)_3—H \quad (VII_3)$$

$$R_1—O—(G)_4—H \quad (VII_4)$$

$$R_1—O—(G)_5—H \quad (VII_5)$$

in the respective molar proportions $a_1$, $a_2$, $a_3$, $a_4$ and $a_5$ such that:

the sum $a_1+a_2+a_3+a_4+a_5$ is equal to 1, and that the sum $a_1+2a_2+3a_3+4a_4+5a_5$ is equal to x; and from 90% to 50% by weight of at least one fatty alcohol of formula (IX):

$$R'''_1—OH, \quad (IX)$$

wherein $R''_1$ represents a radical chosen from the elements of the group consisting of the radicals n-dodecyl, n-tetradecyl, n-hexadecyl, n-octadecyl, n-eicosyl and n-behenyl, where $R''_1$ may be identical to or different from $R_1$;

from 12% to 88% by weight of at least one emulsifying surfactant ($S_2$) which consists of at least one polyglycol polyhydroxystearate represented by formula (XII):

[Chem 4]

(XII)

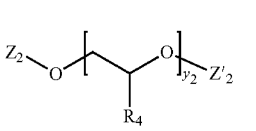

wherein $y_2$ represents an integer greater than or equal to 2 and less than or equal to 50, $R_4$ represents a hydrogen atom, a methyl radical or an ethyl radical, and $Z_2$ represents a radical of formula (XIII):

[Chem 5]

(XIII)

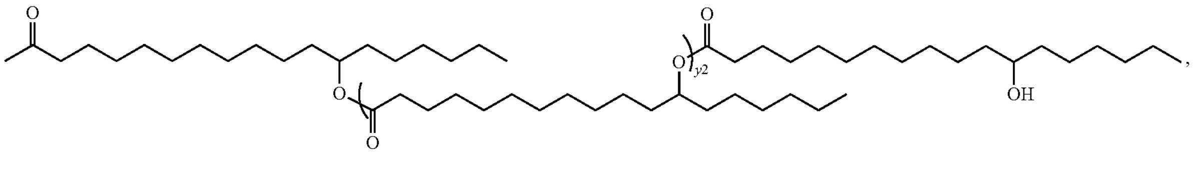

wherein $y'_2$ represents an integer greater than or equal to 0 and less than or equal to 10, more particularly greater than or equal to 1 and less than or equal to 10, and $Z'_2$ represents a radical of formula (XIII) as defined above, where $Z_2'$ may be identical to or different from $Z_2$, or a hydrogen atom.

Regarding the emulsifying surfactant, in formula (VIII) as defined above, the group R1-O— is linked to G via the anomeric carbon of the saccharide residue, so as to form an acetal function.

According to one particular aspect, in the definition of formula (VIII) x, or mean degree of polymerization, represents a decimal number greater than or equal to 1.05 and less than or equal to 2.5, more particularly greater than or equal to 1.05 and less than or equal to 2.0 and more particularly still greater than or equal to 1.25 and less than or equal to 2.0.

According to another particular aspect, the combination of at least one emulsifying surfactant (S1) and at least one emulsifying surfactant (S2) comprises, per 100% of its weight:

from 12% to 88% by weight of at least one emulsifying surfactant ($S_1$) which consists of at least one composition ($C'_2$) comprising, per 100% of its weight:

from 10% to 50% by weight of at least one alkylpolyglycoside composition (C'1) represented by formula (X):

$$R_1—O—(G)_x—H \quad (X)$$

wherein x represents a decimal number between 1.05 and 2.5, G represents the xylose residue and $R_1$ represents the 2-octyldodecyl radical, said composition consisting of a mixture of compounds represented by formulae ($X_1$), ($X_2$), ($X_3$), ($X_4$) and ($X_5$):

$$R_1—O—(G)_1—H \quad (X_1)$$

$$R_1—O—(G)_2—H \quad (X_2)$$

$$R_1—O—(G)_3—H \quad (X_3)$$

$$R_1—O—(G)_4—H \quad (X_4)$$

$$R_1—O—(G)_5—H \quad (X_5)$$

in the respective molar proportions $a_1$, $a_2$, $a_3$, $a_4$ and $a_5$ such that:

the sum $a_1+a_2+a_3+a_4+a_5$ is equal to 1 and that the sum $a_1+2a_2+3a_3+4a_4+5a_5$ is equal to x; and from 90% to 50% by weight of at least one fatty alcohol of formula (XI):

$R'''_1$—OH, (XI)

wherein $R'''_1$ represents the 2-octyldodecyl radical;

from 12% to 88% by weight of at least one emulsifying surfactant ($S_2$) which consists of at least one polyglycol polyhydroxystearate represented by formula (XII):

[Chem 6]

(XII)

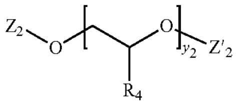

wherein $y_2$ represents an integer greater than or equal to 2 and less than or equal to 50, $R_4$ represents a hydrogen atom, a methyl radical or an ethyl radical, and $Z_2$ represents a radical of formula (XIII):

[Chem 7]

(XIII)

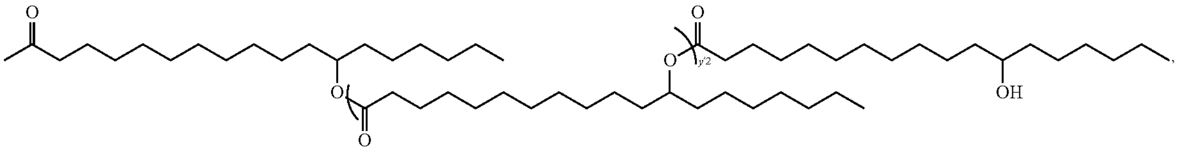

wherein $y'_2$ represents an integer greater than or equal to 0 and less than or equal to 10, more particularly greater than or equal to 1 and less than or equal to 10, and $Z'_2$ represents a radical of formula (XIII) as defined above, where $Z_2'$ may be identical to or different from $Z_2$, or a hydrogen atom.

According to another particular aspect, the composition (E1) for topical use according to the invention has a dynamic viscosity, measured at a temperature of 20° C. using a Brookfield LVT viscometer at a speed of 6 rpm, greater than or equal to 500 mPa·s and less than or equal to 40 000 mPa·s.

Regarding the auxiliary compounds, among the foaming and/or detergent anionic surfactants that may be combined with the composition (E1) for topical use according to the invention, mention may be made of alkali metal salts, alkaline-earth metal salts, ammonium salts, amine salts or amino alcohol salts of alkyl ether sulfates, of alkyl sulfates, of alkylamido ether sulfates, of alkylaryl polyether sulfates, of monoglyceride sulfates, of alpha-olefin sulfonates, of paraffin sulfonates, of alkyl phosphates, of alkyl ether phosphates, of alkyl sulfonates, of alkylamide sulfonates, of alkylaryl sulfonates, of alkyl carboxylates, of alkyl sulfosuccinates, of alkyl ether sulfosuccinates, of alkylamide sulfosuccinates, of alkyl sulfoacetates, of alkyl sarcosinates, of acyl isethionates, of N-acyl taurates, of acyl lactylates, of N-acylated derivatives of amino acids, of N-acylated derivatives of peptides, of N-acylated derivatives of proteins, or of fatty acids.

Among the foaming and/or detergent amphoteric surfactants optionally present in the composition (E1) for topical use according to the invention, mention may be made of alkylbetaines, alkylamidobetaines, sultaines, alkylamidoalkylsulfobetaines, imidazoline derivatives, phosphobetaines, amphopolyacetates and amphopropionates.

Among the foaming and/or detergent cationic surfactants optionally present in the composition (E1) for topical use according to the invention, mention may be made particularly of quaternary ammonium derivatives.

Among the foaming and/or detergent nonionic surfactants optionally present in the composition (E1) for topical use according to the invention, mention may be made more particularly of alkylpolyglycosides containing a linear or branched, saturated or unsaturated aliphatic radical and comprising from 8 to 12 carbon atoms; castor oil derivatives, polysorbates, coconut kernel amides and N-alkylamines.

As examples of thickening and/or gelling surfactants optionally present in the composition (E1) for topical use according to the invention, mention may be made of:

optionally alkoxylated fatty esters of alkylpolyglycosides, and most particularly ethoxylated esters of methylpolyglucoside such as PEG 120 methyl glucose trioleate and PEG 120 methyl glucose dioleate sold, respectively, under the names Glucamate™ LT and Glumate™ DOE120;

alkoxylated fatty esters such as the PEG 150 pentaerythrityl tetrastearate sold under the name Crothix™ DS53, or PEG 55 propylene glycol oleate sold under the name Antil™ 141;

fatty-chain polyalkylene glycol carbamates such as PPG 14 laureth isophoryl dicarbamate sold under the name Elfacos™ T211, or PPG 14 palmeth 60 hexyl dicarbamate sold under the name Elfacos™ GT2125.

As examples of emulsifying surfactants optionally present in the composition (E1) for topical use according to the invention, mention may be made of nonionic surfactants, anionic surfactants and cationic surfactants.

As examples of emulsifying nonionic surfactants optionally present in the composition (E1) for topical use according to the invention, ethoxylated castor oil and ethoxylated hydrogenated castor oil, for example the product sold under the name Simulsol™ 989; compositions comprising glycerol stearate and stearic acid poly(ethoxylated) with between 5 mol and 150 mol of ethylene oxide, for example the composition comprising stearic acid (ethoxylated) with 135 mol of ethylene oxide and glycerol stearate sold under the name Simulsol™ 165; ethoxylated sorbitan esters, for example the products sold under the name Montanox™; ethoxylated mannitan esters; sucrose esters; methyl glucoside esters.

As examples of emulsifying anionic surfactants that may be present in the composition (E1) for topical use according to the invention, mention may be made of decyl phosphate, cetyl phosphate sold under the name Amphisol™, glyceryl stearate citrate; cetearyl sulfate; the arachidyl/behenyl phosphates and arachidyl/behenyl alcohols composition sold under the name Sensanov™ WR; soaps, for example sodium stearate or triethanolammonium stearate, or N-acylated derivatives of amino acids which are salified, for instance stearoyl glutamate.

As examples of emulsifying cationic surfactants optionally present in the composition (E1) for topical use according to the invention, mention may be made of amine oxides, quaternium-82, cetyltrimethylammonium chloride, hexadecyltrimethylammonium bromide, cetylpyridinium chloride, benzalkonium chloride, benzethonium chloride, and the surfactants described in document WO96/00719 and mainly those wherein the fatty chain comprises at least 16 carbon atoms.

As examples of opacifying agents and/or pearlescent agents optionally present in the composition (E1) for topical use according to the invention, mention may be made of sodium palmitate, sodium stearate, sodium hydroxystearate, magnesium palmitate, magnesium stearate, magnesium hydroxystearate, ethylene glycol monostearate, ethylene glycol distearate, polyethylene glycol monostearate, polyethylene glycol distearate and fatty alcohols comprising from 12 to 22 carbon atoms.

As examples of texturing agents optionally present in the composition (E1) for topical use according to the invention, mention may be made of N-acylated derivatives of amino acids, for example lauroyl lysine sold under the name Aminohope™ LL, octenyl starch succinate sold under the name Dryflo™, myristyl polyglucoside sold under the name Montanov 14, cellulose fibers, cotton fibers, chitosan fibers, talc, sericite and mica.

As examples of solvents and co-solvents optionally present in the composition (E1) for topical use according to the invention, mention may be made of water, organic solvents, for example glycerol, diglycerol, glycerol oligomers, ethylene glycol, propylene glycol, butylene glycol, hexylene glycol, diethylene glycol, xylitol, erythritol, sorbitol, water-soluble alcohols such as ethanol, isopropanol or butanol, mixtures of water and of said organic solvents, propylene carbonate, ethyl acetate, benzyl alcohol and dimethyl sulfoxide (DMSO).

As examples of agents for improving the skin penetration optionally present in the composition (E1) for topical use according to the invention, mention may be made of glycol ethers, for instance ethylene glycol monomethyl ether, ethylene glycol monoethyl ether, ethylene glycol monopropyl ether, ethylene glycol monoisopropyl ether, ethylene glycol monobutyl ether, ethylene glycol monophenyl ether, ethylene glycol monobenzyl ether, diethylene glycol monomethyl ether, diethylene glycol monoethyl ether and diethylene glycol mono-n-butyl ether, diethylene glycol monoethyl ether (or Transcutol-P), fatty acids such as oleic acid, fatty acid esters of glycerol, for instance glyceryl behenate, glyceryl palmitostearate, behenoyl macroglycerides, polyoxyethylene-2-stearyl ether, polyoxyethylene-2-oleyl ether, terpenes, for instance D-limonene, and essential oils, for instance the essential oil of eucalyptus.

As examples of thickening and/or gelling agents optionally present in the composition (E1) for topical use according to the invention, mention may be made of polysaccharides consisting only of monosaccharides, such as glucans or glucose homopolymers, glucomannoglucans, xyloglycans, galactomannans of which the degree of substitution (DS) of the D-galactose units on the main D-mannose chain is between 0 and 1, and more particularly between 1 and 0.25, such as galactomannans originating from cassia gum (DS=1/5), locust bean gum (DS=¼), tara gum (DS=⅓), guar gum (DS=½) or fenugreek gum (DS=1).

As examples of thickening and/or gelling agents optionally present in the composition (E1) for topical use according to the invention, mention may be made of polysaccharides consisting of monosaccharide derivatives, such as sulfated galactans and more particularly carrageenans and agar, uronans and more particularly algins, alginates and pectins, heteropolymers of monosaccharides and uronic acids, and more particularly xanthan gum, gellan gum, gum arabic exudates and karaya gum exudates, and glucosaminoglycans.

As examples of thickening and/or gelling agents optionally present in the composition (E1) for topical use according to the invention, mention may be made of cellulose, cellulose derivatives such as methyl cellulose, ethyl cellulose, hydroxypropyl cellulose, silicates, starch, hydrophilic starch derivatives, and polyurethanes.

As examples of stabilizers optionally present in the composition (E1) for topical use according to the invention, mention may be made of microcrystalline waxes, and more particularly of ozokerite, and mineral salts such as sodium chloride or magnesium chloride.

As examples of thermal or mineral waters which can be combined with the composition (E1) for topical use according to the invention, mention may be made of thermal or mineral waters having a mineralization of at least 300 mg/l, in particular Avene water, Vittel water, Vichy basin water, Uriage water, La Roche-Posay water, La Bourboule water, Enghien-les-Bains water, Saint-Gervais-les-Bains water, Néris-les-Bains water, Allevard-les-Bains water, Digne water, Maizières water, Neyrac-les-Bains water, Lons-le-Saunier water, Rochefort water, Saint Christau water, Les Fumades water and Tercis-les-Bains water.

As examples of active agents which can be combined with the composition (E1) for topical use according to the invention, mention may be made of substances or compositions which provide a beneficial effect to the human or animal subject.

Mention may be made, as examples of deodorants optionally present in the composition (E1) for topical use which is a subject of the present invention, of alkali metal silicates, zinc salts, such as zinc sulfate, zinc gluconate, zinc chloride or zinc lactate; quaternary ammonium salts, such as cetyltrimethylammonium salts or cetylpyridinium salts; glycerol derivatives, such as glyceryl caprate, glyceryl caprylate or polyglyceryl caprate; 1,2-decanediol, 1,3-propanediol; salicylic acid; sodium bicarbonate; cyclodextrins; metal zeolites; Triclosan™; aluminum bromohydrate, aluminum chlorohydrates, aluminum chloride, aluminum sulfate, aluminum zirconium chlorohydrates, aluminum zirconium trichlorohydrate, aluminum zirconium tetrachlorohydrate, aluminum zirconium pentachlorohydrate, aluminum zirconium octachlorohydrate, aluminum sulfate, sodium aluminum lactate, or complexes of aluminum chlorohydrate and of glycol, such as the complex of aluminum chlorohydrate and propylene glycol, the complex of aluminum dichlorohydrate and propylene glycol, the complex of aluminum sesquichlorohydrate and propylene glycol, the complex of aluminum chlorohydrate and polyethylene glycol, the complex of aluminum dichlorohydrate and polyethylene glycol or the complex of aluminum sesquichlorohydrate and polyethylene glycol.

As examples of antioxidants that may be present in composition (E1) for topical use which is a subject of the present invention, mention may be made of EDTA and salts thereof, citric acid, tartaric acid, oxalic acid, BHA (butylhydroxyanisole), BHT (butylhydroxytoluene), tocopherol derivatives such as tocopheryl acetate, mixtures of antioxidant compounds such as Dissolvine GL 47S (INCI name: Tetrasodium Glutamate Diacetate).

Among the active ingredients that may be included in the composition (E1) for topical use which is a subject of the present invention, mention may be made of:

vitamins and their derivatives, in particular their esters, such as retinol (vitamin A) and its esters (retinyl palmitate, for example), ascorbic acid (vitamin C) and its esters, sugar derivatives of ascorbic acid (such as ascorbyl glucoside), tocopherol (vitamin E) and its esters (such as tocopherol acetate), vitamins B3 or B10 (niacinamide and its derivatives); compounds showing a soothing action, in particular Sepicalm™ S, allantoin and bisabolol; anti-inflammatory agents; compounds showing a moisturizing action, such as urea, hydroxyureas, glycerol glucoside, diglycerol glucoside, polyglyceryl glucosides, glycerol, diglycerol or xylityl polyglucoside, sold under the brand name Aquaxyl™; plant extracts rich in polyphenols, such as grape extracts, pine extracts, wine extracts or olive extracts; compounds showing a slimming or lipolytic action, such as caffeine or its derivatives, Adiposlim™, Adipoless™ or fucoxanthin; N-acylated proteins; N-acylated peptides, such as Matrixil™; N-acylated amino acids; partial hydrolysates of N-acylated proteins; amino acids; peptides; total hydrolysates of proteins; soybean extracts, for example Raffermine™; wheat extracts, for example Tensine™ or Gliadine™; plant extracts, such as plant extracts rich in tannins, plant extracts rich in isoflavones or plant extracts rich in terpenes; extracts of freshwater or marine algae; extracts of marine plants; marine extracts in general, such as corals; essential waxes; bacterial extracts; ceramides; phospholipids; compounds showing an antimicrobial action or a purifying action, such as Lipacide™ C8G, Lipacide™ UG, Sepicontrol™ A5, Octopirox™ or Sensiva™ SC50; compounds showing an energizing or stimulating property, such as Physiogenyl™, or panthenol and its derivatives, such as Sepicap™ MP; antiaging active ingredients, such as Sepilift™ DPHP, Lipacide™ PVB, Sepivinol™, Sepivital™, Manoliva™, Phyto-Age™, Timecode™ or Survicode™; antiphotoaging active ingredients; active ingredients which protect the integrity of the dermoepidermal junction; active ingredients which increase the synthesis of the components of the extracellular matrix, such as collagen, elastins or glycosaminoglycans; active ingredients which act favorably on chemical cell communication, such as cytokines, or physical cell communication, such as integrins; active ingredients which create a feeling of "heating" on the skin, such as activators of cutaneous microcirculation (such as nicotinic acid derivatives) or products which create a feeling of "coolness" on the skin (such as menthol and derivatives); active ingredients which improve cutaneous microcirculation, for example venotonics; draining active ingredients; active ingredients having a decongestant purpose, such as extracts of ginko biloba, ivy, horse chestnut, bamboo, ruscus, butcher's broom, *Centalla asiatica*, fucus, rosemary or willow; agents for tanning or browning the skin, such as, for example, dihydroxyacetone (DHA), erythrulose, mesotartaric aldehyde, glutaraldehyde, glyceraldehyde, alloxan, ninhydrin, plant extracts, such as, for example, extracts of red woods of the genus *Pterocarpus* and of the genus *Baphia*, such as *Pteropcarpus santalinus, Pterocarpus osun, Pterocarpus soyauxii, Pterocarpus erinaceus, Pterocarpus indicus* or *Baphia nitida*, such as those described in the European patent application EP 0 971 683; agents known for their action in facilitating and/or accelerating the tanning and/or browning of human skin, and/or for their action in coloring human skin, such as, for example, carotenoids (and more particularly β-carotene and γ-carotene), the product sold under the brand name "Carrot oil" (INCI name: *Daucus carrota, Helianthus annuus* sunflower oil) by the company Provital, which contains carotenoids, vitamin E and vitamin K; tyrosine and/or derivatives thereof, known for their effect on accelerating the tanning of human skin in combination with exposure to ultraviolet radiation, for instance the product sold under the brand name SunTan Accelerator™ by the company Provital, which contains tyrosine and riboflavins (vitamin B), the tyrosine and tyrosinase complex sold under the brand name Zymo Tan Complex by the company Zymo Line, the product sold under the brand name Melano-Bronze™ (INCI name: Acetyl tyrosine, monk's pepper extract (*Vitex agnus-castus*)) by the company Mibelle, which contains acetyl tyrosine, the product sold under the brand name Unipertan VEG-24/242/2002 (INCI name: Butylene glycol and acetyl tyrosine and hydrolyzed plant protein and adenosine triphosphate) by the company Unipex, the product sold under the brand name Try-Excell™ (INCI name: Oleoyl tyrosine and *Luffa cylindrica* (seed) oil and oleic acid) by the company Sederma, which contains extracts of marrow seeds (or loofah oil), the product sold under the brand name Actibronze™ (INCI name: Hydrolyzed wheat protein and acetyl tyrosine and copper gluconate) by the company Alban Muller, the product sold under the brand name Tyrostan™ (INCI name: Potassium caproyl tyrosine) by the company Synerga, the product sold under the brand name Tyrosinol (INCI name: Sorbitan isostearate, glyceryl oleate, caproyl tyrosine) by the company Synerga, the product sold under the brand name InstaBronze™ (INCI name: Dihydroxyacetone and acetyl tyrosine and copper gluconate) sold by the company Alban Muller, the product sold under the brand name Tyrosilane (INCI name: Methylsilanol and acetyl tyrosine) by the company Exymol; peptides known for their effect on activating melanogenesis, for instance the product sold under the brand name Bronzing SF peptide powder (INCI name: Dextran and octapeptide-5) by the company Infinitec Activos, the product sold under the brand name Melitane (INCI name: Glycerin and aqua and dextran and acetyl hexapeptide-1) comprising acetyl hexapeptide-1 known for its alpha-MSH-agonist action, the product sold under the brand name Melatimes Solutions™ (INCI name: Butylene glycol, palmitoyl tripeptide-40) by the company Lipotec, sugars and sugar derivatives, for example the product sold under the brand name Tanositol™ (INCI name: Inositol) by the company Provital, the product sold under the brand name Thalitan™ (or Phycosaccharide™ AG) by the company Codif International (INCI name: Aqua and hydrolyzed algin (*Laminaria digitata*) and magnesium sulfate and manganese sulfate) containing an oligosaccharide of marine origin (guluronic acid and mannuronic acid chelated with magnesium and manganese ions), the product sold under the brand name Melactiva™ (INCI name: Maltodextrin, *Mucuna pruriens* seed extract) by the company Alban Muller, flavonoid-rich compounds, for instance the product sold under the brand name Biotanning (INCI name: Hydrolyzed citrus *Aurantium dulcis* fruit extract) by the company Silab and known for being rich in lemon flavonoids (of hesperidin type).

As examples of sunscreens optionally present in composition ($E_1$) for topical use which is a subject of the present invention, mention may be made of all those listed in the modified cosmetics directive 76/768/EEC, annex VII.

Among the organic sunscreens optionally present in composition ($E_1$) for topical use which is a subject of the present invention, mention may be made of:

- benzoic acid derivatives, such as para-aminobenzoic acids (PABAs), notably monoglyceryl esters of PABA, ethyl esters of N,N-propoxy PABA, ethyl esters of N,N-diethoxy PABA, ethyl esters of N,N-dimethyl PABA, methyl esters of N,N-dimethyl PABA, butyl esters of N,N-dimethyl PABA;
- anthranilic acid derivatives, such as homomenthyl-N-acetyl anthranilate;
- salicylic acid derivatives, such as amyl salicylate, homomenthyl salicylate, ethylhexyl salicylate, phenyl salicylate, benzyl salicylate, p-isopropylphenyl salicylate;
- cinnamic acid derivatives, such as ethylhexyl cinnamate, ethyl-4-isopropyl cinnamate, methyl-2,5-diisopropyl cinnamate, p-methoxypropyl cinnamate, p-methoxyisopropyl cinnamate, p-methoxyisoamyl cinnamate, p-methoxyoctyl cinnamate (p-methoxy 2-ethylhexyl cinnamate), p-methoxy 2-ethoxyethyl cinnamate, p-methoxycyclohexyl cinnamate, ethyl-α-cyano-β-phenyl cinnamate, 2-ethylhexyl-α-cyano-β-phenyl cinnamate, glyceryl di-para-methoxy mono-2-ethylhexanoyl cinnamate;
- benzophenone derivatives such as 2,4-dihydroxybenzophenone, 2,2'-dihydroxy-4-methoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone 5-sulfonate, 4-phenylbenzophenone, 2-ethylhexyl-4'-phenylbenzophenone 2-carboxylate, 2-hydroxy-4-n-octyloxybenzophenone, 4-hydroxy-3-carboxybenzophenone; 3-(4'-methylbenzylidene)-d,l-camphor, 3-(benzylidene)-d,l-camphor, camphorbenzalkonium methosulfate; urocanic acid, ethyl urocanate; the family of sulfonic acid derivatives such as 2-phenylbenzimidazole-5-sulfonic acid and salts thereof;
- triazine derivatives such as hydroxyphenyl triazine, (ethylhexyloxyhydroxyphenyl)(4-methoxyphenyl)triazine, 2,4,6-trianilino(p-carbo-2'-ethylhexyl-1'-oxy)-1,3,5-triazine, 4,4-((6-(((1,1-dimethylethyl)amino)carbonyl) phenyl)amino)-1,3,5-triazine-2,4-diyldiimino)bis(2-ethylhexyl) benzoate, 2-phenyl-5-methylbenzoxazole, 2,2'-hydroxy-5-methylphenylbenzotriazole, 2-(2'-hydroxy-5'-t-octylphenyl)benzotriazole, 2-(2'-hydroxy-5'-methyphenyl)benzotriazole; dibenzazine; dianisoylmethane, 4-methoxy-4"-t-butylbenzoylmethane; 5-(3,3-dimethyl-2-norbornylidene)-3-pentan-2-one;
- diphenylacrylate derivatives, such as 2-ethylhexyl 2-cyano-3,3-diphenyl-2-propenoate or ethyl 2-cyano-3,3-diphenyl-2-propenoate;
- polysiloxanes, such as benzylidene siloxane malonate.

Among the inorganic sunscreens, also called "mineral screens", optionally present in the composition ($E_1$) for topical use which is a subject of the present invention, mention may be made of titanium oxides, zinc oxides, cerium oxide, zirconium oxide, yellow, red or black iron oxides, and chromium oxides. These inorganic screening agents may or may not be micronized, may or may not have undergone surface treatments and may optionally be presented in the form of aqueous or oily predispersions.

The composition according to the invention and as defined above is obtained by performing the preparation process comprising the following steps:

- A step a) of preparing the fatty phase (A2) by mixing all of the elements constituting it in the desired proportions. This mixing step is generally performed at a temperature of greater than or equal to 20° C. and less than or equal to 80° C., more particularly greater than or equal to 25° C. and less than or equal to 80° C., and even more particularly greater than or equal to 30° C. and less than or equal to 80° C.; it is performed with mechanical stirring at a moderate speed of greater than or equal to 50 rpm and less than or equal to 100 rpm;
- A step b) of preparing the aqueous phase ($A_1$) from all of the elements constituting it in the desired proportions. This mixing step is generally carried out at a temperature of greater than or equal to 20° C. and less than or equal to 80° C., more particularly of greater than or equal to 20° C. and less than or equal to 60° C. and more particularly still of greater than or equal to 20° C. and less than or equal to 40° C.; it is carried out under mechanical stirring at a moderate speed of greater than or equal to 500 rpm and less than or equal to 3000 rpm. In particular, the aqueous phase ($A_1$) obtained on conclusion of step b) has a dynamic viscosity, measured at 20° C. using a Brookfield LV viscometer at a speed of 6 rpm, of greater than or equal to 200 mPa·s and less than or equal to 40 000 mPa·s, more particularly greater than or equal to 1000 mPa·s and less than or equal to 40 000 mPa·s, and even more particularly greater than or equal to 2000 mPa·s and less than or equal to 40 000 mPa·s;
- A step c) during which the fatty phase (A2) is added to the aqueous phase ($A_1$) at a temperature of greater than or equal to 20° C. and less than or equal to 80° C., more particularly greater than or equal to 20° C. and less than or equal to 60° C., and more particularly still greater than or equal to 20° C. and less than or equal to 40° C., with mechanical stirring at a moderate speed of greater than or equal to 50 rpm and less than or equal to 400 rpm, so as to obtain the composition according to the invention.

DESCRIPTION OF THE PREFERRED EMBODIMENTS

The examples that follow illustrate the invention without, however, limiting it.

Preparation and Evaluation of Emulsions According to the Invention and of Comparative Emulsions 1) Preparation of the Emulsions According to the Invention and of the Comparative Emulsions Three emulsions according to the invention, denoted ($F_1$) to ($F_3$), and four comparative emulsions, denoted ($F'_1$) to ($F'_4$), the proportions by weight of the constituents of which are recorded in table 1 below, the contents by weight of the polyelectrolytes being indicated as a percentage of polymeric solids, are prepared by performing the following process.

The constituents of the fatty phase are introduced successively into a beaker, mixed and brought to a temperature of 20° C. after an 80° C. heating step; the mixing is performed using a mechanical stirrer equipped with a propeller-type stirring spindle at a speed of 100 rpm.

The constituents of the dispersed phase are mixed at ambient temperature in a beaker using a mechanical stirrer at a speed of 2000 rpm and the thickener is then added gradually. The stirring is maintained for a duration which makes it possible to obtain a phase which is in the form of a homogeneous gel. The fatty phase is added in one go to the gel at ambient temperature and at a moderate stirring speed (75 to 300 rpm) using a stirrer equipped with an anchor-type spindle. This stirring is then maintained for 10 minutes and no cooling step is necessary.

2.2 Characterization of the Direction of the Emulsions ($F_1$) to ($F_3$) According to the Invention and of the Comparative Emulsions ($F'_1$) to ($F'_3$)

The conductivity ($\sigma$) of the emulsions ($F_1$) to ($F_3$) according to the invention and of the emulsions ($F'_1$) to ($F'_3$) is measured at 25° C., after a period of storage of said emulsions of one day in an insulated climatic chamber regulated at a temperature of 25° C., by means of an LF 196™ brand conductivity meter from the company WTW equipped with a TetraCon™ 96 electrode. For a given emulsion, $(\sigma) \leq 0.5\ \mu S \cdot cm^{-1}$, the emulsion is considered to be

TABLE 1

| | ($F_1$) | ($F_2$) | ($F_3$) | ($F'_1$) | ($F'_2$) | ($F'_3$) | ($F'_4$) |
|---|---|---|---|---|---|---|---|
| Continuous fatty phase | | | | | | | |
| Lanol ™ 2681 (1) | 5% | 5% | 5% | 5% | 5% | 5% | 5% |
| Sepineo ™ SE 68(2) | 0.4% | 0% | 0% | 0% | 0% | 0% | 0% |
| Sepicide ™ HB (3) | 1% | 1% | 1% | 1% | 1% | 1% | 1% |
| Simaline ™WO(4) | 1.1% | 1.1% | 1.1% | 1.1% | 1.1% | 1.1% | 1.1% |
| Montane ™80(6) | 0% | 0% | 0% | 1.2% | 1.2% | 1.2% | 1.2% |
| Montanov ™202(8) | 0% | 0.4% | 0% | 0% | 0% | 0% | 0% |
| Fluidanov ™20X(9) | 0% | 0% | 0.4% | 0% | 0% | 0% | 0% |
| Dispersed phase | | | | | | | |
| Sepineo ™P600(5) | 2% | 2% | 2% | 2% | 2% | 2% | 2% |
| PEG-400(7) | 0% | 0% | 0% | 0% | 0% | 0% | 50% |
| Glycerol | 0% | 0% | 0% | 0% | 0% | 60% | 0% |
| Water | 0% | 0% | 0% | 0% | 10.5%(*) | 30.5%(*) | 40.5%(*) |
| 1,2-propanediol | 90.5% | 90.5% | 90.5% | 90.5% | 80% | 0% | 0% |

(1) Lanol ™ 2681, or Coco-Caprylate/Caprate.

(2) Sepineo ™ SE 68 is a mixture comprising, per 100% of its weight, from 78% to 85% by weight of a mixture of n-hexadecanol and n-octadecanol, and from 15% to 22% by weight of a mixture of n-hexadecyl glucoside with a mean degree of polymerization of 1.20 and n-octadecyl glucoside with a mean degree of polymerization of 1.20, used as emulsifying agent.

(3) Sepicide ™ HB is a mixture of phenoxyethanol, methylparaben, ethylparaben, butylparaben and n-propylparaben, used as a preserving agent.

(4) Simaline ™ WO, or PEG 30 Dipolyhydroxystearate, is an emulsifying surfactant.

(5) Sepineo ™ P600 is a self-invertible inverse latex comprising, per 100% of its weight, between 30% and 40% by weight of a crosslinked copolymer of acrylamide and of sodium acryloyldimethyltaurate, used as a thickening agent.

(6) Montane ™ 80 is a composition comprising sorbitan monooleate, used as water-in-oil type emulsifying agent.

(7) PEG-400 is a polyethylene glycol with a molecular weight of approximately 400 $g \cdot mol^{-1}$.

(8) Montanov ™ 202 is a mixture comprising, per 100% of its weight, from 80% to 90% by weight of a mixture of arachidyl alcohol and behenyl alcohol, and from 10% to 20% by weight of arachidyl polyglucosides with an average degree of polymerization of 1.20, used as an emulsifying agent.

(9) Fluidanov ™ 20X is a mixture comprising, per 100% of its weight, from 70% to 90% by weight of 2-octyl-1-dodecanol and from 10% to 30% by weight of 2-octyl-1-dodecanyl polyxyloside.

(*) minimum weight proportion of water that could be added to the respective comparative emulsions ($F_2$), ($F'_3$), ($F'_4$) without either obtaining gelation preventing stirring of said emulsion, or obtaining an emulsion exhibiting a heterogeneous appearance that persists despite the stirring phases of the preparation process, or a form for which the dispersed phase is the fatty phase.

2 Demonstration of the Properties of Emulsions ($F_1$) to ($F_3$) According to the Invention and of Comparative Emulsions ($F'_1$) to ($F'_4$)

2.1 Characterization of the Appearance and Viscosity of Emulsions ($F_1$) to ($F_3$) According to the Invention and of Comparative Emulsions ($F'_1$) to ($F'_4$)

The emulsions ($F_1$) to ($F_3$) and ($F'_1$) to ($F'_4$) obtained according to the process described above are then stored in an insulated climatic chamber regulated at a temperature of 25° C. for 3 months. After the conclusion of this period of three months, the appearance (APP) of each emulsion prepared is observed and the dynamic viscosity ($\mu$) of each emulsion is measured (in mPas) by means of a viscometer at 25° C. (Brookfield LVT, speed 6).

An aliquot of these same emulsions ($F_1$) to ($F_3$) and ($F'_1$) to ($F'_4$) obtained according to the process described above is also stored in an insulated climatic chamber regulated at a temperature of 45° C. for three months. After the conclusion of this period of three months, the appearance (APP) of each emulsion prepared is observed and the dynamic viscosity ($\mu$) of each emulsion is measured (in mPas) by means of a viscometer at 25° C. (Brookfield LVT, speed 6).

non-conductive and consequently the external phase is not the phase based on 1,2-propanediol or on glycerol or on PEG-400, but the oily phase.

Indeed, the conductivity, measured at 25° C., of 1,2-propanediol is equal to $4400\ \mu S \cdot cm^{-1}$, that of glycerol is $6400\ \mu S \cdot cm^{-1}$.

For a given emulsion, $(\sigma) > 0.5\ \mu S \cdot cm^{-1}$, the emulsion is considered to be conductive and consequently the external phase is considered not to be the oily phase but the glycolic phase. The term "glycolic phase" means the phase based on 1,2-propanediol or on glycerol or on PEG-400.

This same measurement of the conductivity of the emulsions ($F_1$) to ($F_3$) according to the invention and of the comparative emulsions ($F'_1$) to ($F'_3$) is measured at 25° C. after three months at 25° C., and after three months at 45° C.

2.3 Results Obtained for the Emulsions ($F_1$) to ($F_3$) According to the Invention and for the Comparative Emulsions ($F'_1$) to ($F'_3$)

The evaluation methods described in sections 2.1 and 2.2 were applied to the emulsions ($F_1$) to ($F_3$) according to the invention and to the comparative emulsions ($F'_1$) to ($F'_3$). The results obtained are recorded in table 2 below.

TABLE 2

| | (F1) | (F2) | (F3) | (F'1) | (F'2) | (F'3) | (F'4) |
|---|---|---|---|---|---|---|---|
| (APP) at 1 day (visual) | Homogeneous liquid | Homogeneous liquid | Homogeneous liquid | Homogeneous liquid | Homogeneous liquid | Homogeneous liquid | Homogeneous liquid |
| (σ) at 1 day at 25° C. | ≤0.5 $\mu S \cdot cm^{-1}$ | ≤0.5 $\mu S \cdot cm^{-1}$ | ≤0.5 $\mu S \cdot cm^{-1}$ | >0.5 $\mu S \cdot cm^{-1}$ | ≤0.5 $\mu S \cdot cm^{-1}$ | ≤0.5 $\mu S \cdot cm^{-1}$ | ≤0.5 $\mu S \cdot cm^{-1}$ |
| Dispersed phase | Glycolic phase | Glycolic phase | Glycolic phase | Fatty phase | Glycolic phase | Glycolic phase | Glycolic phase |
| (APP) at 7 days at 25° C. | Homogeneous liquid | Homogeneous liquid | Homogeneous liquid | Homogeneous liquid | Homogeneous liquid | Homogeneous liquid | Homogeneous liquid |
| (σ) at 3 months at 25° C. | ≤0.5 $\mu S \cdot cm^{-1}$ | ≤0.5 $\mu S \cdot cm^{-1}$ | ≤0.5 $\mu S \cdot cm^{-1}$ | >0.5 $\mu S \cdot cm^{-1}$ | ≤0.5 $\mu S \cdot cm^{-1}$ | ≤0.5 $\mu S \cdot cm^{-1}$ | ≤0.5 $\mu S \cdot cm^{-1}$ |
| (μ) at 3 months at 25° C. | 43 000 mPas | 44 200 mPas | 48 000 mPas | not measured | not measured | not measured | not measured |
| (APP) at 3 months at 45° C. | Homogeneous liquid | Homogeneous liquid | Homogeneous liquid | Homogeneous liquid | Homogeneous liquid | Homogeneous liquid | Homogeneous liquid |
| (σ) at 3 months at 45° C. | ≤0.5 $\mu S \cdot cm^{-1}$ | ≤0.5 $\mu S \cdot cm^{-1}$ | ≤0.5 $\mu S \cdot cm^{-1}$ | >0.5 $\mu S \cdot cm^{-1}$ | ≤0.5 $\mu S \cdot cm^{-1}$ | ≤0.5 $\mu S \cdot cm^{-1}$ | ≤0.5 $\mu S \cdot cm^{-1}$ |

2.4 Analysis of the Results

The emulsions ($F_1$) to ($F_3$) according to the invention are therefore characterized by:

- a stability of their form, of the type based on 1,2-propanediol dispersed in oil, after storage for 3 months at a temperature of 25° C.; the appearance observed after this storage period is still homogeneous;
- a stability of their form, of the type based on 1,2-propanediol dispersed in oil, after storage for 3 months at a temperature of 45° C.; the appearance observed after this storage period is still homogeneous;

The comparative emulsion ($F'_1$) comprising sorbitan monooleate as oil-in-water lipophilic surfactant does not make it possible to obtain an emulsion wherein the dispersed phase is the phase based on 1,2-propanediol.

The comparative emulsions ($F'_2$), ($F'_3$) and ($F'_4$), also comprising sorbitan monooleate as oil-in-water lipophilic surfactant, make it possible to obtain an emulsion wherein the dispersed phase is the phase based on 1,2-propanediol, but a minimum amount of water is necessary. Unexpectedly, the use of the water-in-oil emulsifying surfactant, sorbitan monooleate, does not make it possible to obtain an emulsion wherein the dispersed phase is the phase based on 1,2-propanediol without the addition of water (F'2 compared to F'1); the same is true with the use of other polyols commonly used to prepare formulations for topical application (F'3 and F'4).

The invention claimed is:

1. A composition (E1) in a form suitable for topical use comprising a dispersed gelled phase (A1) free of added water and dispersed in a continuous phase (A2), with:

the dispersed gelled phase (A1) comprising, per 100% of its weight, from 0.5% to 10% by weight of a cross-linked anionic polyelectrolyte (AP1) in the form of a crosslinked copolymer of acrylamide and of sodium acryloyldimethyltaurate, and from 90% to 99.5% by weight of at least one diol selected from the group consisting of 1,2-propanediol, 1,2-butanediol, 1,3-butanediol, 1,2-pentanediol, 1,2-hexanediol and 2-methyl 2,4-pentanediol, and the continuous phase (A2) being a fatty phase comprising at least one oil, at least one emulsifying surfactant (S1) and at least one emulsifying surfactant (S2), wherein the emulsifying surfactant (S1) comprises at least one composition (C2) comprising, per 100% of its weight:

from 10% to 50% by weight of at least one alkylpolyglycoside composition (C1) represented by formula (VII):

$$R_1—O—(G)_x—H, \qquad (VII)$$

wherein x represents a decimal number between 1.05 and 2.5, G represents the glucosyl or α,β-D-glucopyranosyl radical, obtained from the removal of the hemiacetal hydroxyl group from α,β-D-glucopyranose, and $R_1$ represents a radical selected from the group consisting of the radicals n-dodecyl, n-tetradecyl, n-hexadecyl, n-octadecyl, n-eicosyl and n-behenyl, said composition consisting of a mixture of compounds represented by formulae (VII1), (VII2), (VII3), (VII4) and (VII5):

$$R1—O—(G)1—H \qquad (VII1)$$

$$R1—O—(G)2—H \qquad (VII2)$$

$$R1—O—(G)3—H \qquad (VII3)$$

$$R1—O—(G)4—H \qquad (VII4)$$

$$R1—O—(G)5—H \qquad (VII5)$$

in the respective molar proportions $a_1$, $a_2$, $a_3$, $a_4$ and $a_5$ such that:

the sum $a_1+a_2+a_3+a_4+a_5$ is equal to 1 and that the sum $a_1+2a_2+3a_3+4a_4+5a_5$ is equal to x; and from 90% to 50% by weight of at least one fatty alcohol of formula (VIII):

(VIII)

$$R''_1—OH,$$

wherein R"1 represents a radical selected from the group consisting of the radicals n-dodecyl, n-tetradecyl, n-hexadecyl, n-octadecyl, n-eicosyl and n-behenyl, where $R''_1$ may be identical to or different from $R_1$; and wherein the emulsifying surfactant (S2) comprises at least one polyglycol polyhydroxystearate represented by the formula (XII):

(XII)

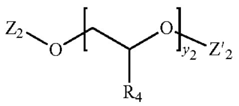

wherein $y^2$ represents an integer greater than or equal to 2 and less than or equal to 50, $R_4$ represents a hydrogen atom, methyl radical or an ethyl radical, and $Z_2$ represents a radical of formula (XIII):

(XIII)

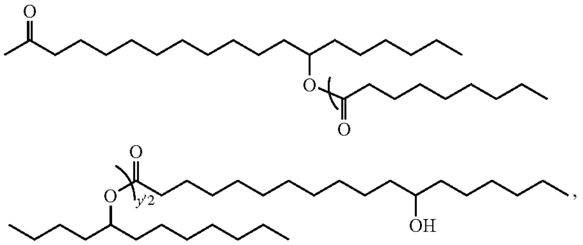

wherein $y'_2$ represents an integer greater than or equal to 0 and less than or equal to 10, and $Z'_2$ represents a radical of formula (XIII) as defined above, where $Z'_2$ may be identical to or different from $Z_2$, or a hydrogen atom;

wherein said composition (E1) comprises, per 100% of its weight:

from 60% to 98% by weight of the dispersed gelled phase (A1), and from 2% to 40% by weight of the continuous fatty phase (A2); and wherein said composition (E1) remains homogeneous at a temperature greater than or equal to 20° C. and less than or equal to 25° C. after storage for at least three months, as well as at 45° C. after storage for at least three months.

2. The composition (E1) as claimed in claim 1, further comprising one or more auxiliary compounds selected from the group consisting of foaming and/or detergent surfactants, thickening and/or gelling surfactants, thickening and/or gelling agents, stabilizers, film-forming compounds, solvents and cosolvents, hydrotropic agents, plasticizers, emulsifiers and co-emulsifiers, opacifiers, self-tanning agents, nacreous agents, superfatting agents, sequestrants, chelating agents, antioxidants, fragrances, essential oils, preserving agents, conditioning agents, deodorants, bleaching agents intended for bleaching bodily hair and the skin, active ingredients intended to provide a treating and/or protective action to the skin or the hair, sunscreens, mineral fillers or pigments, particles that give a visual effect or that are intended for encapsulating active agents, exfoliant particles, texturing agents, optical brighteners and insect repellents.

3. The composition (E1) as claimed in claim 2, comprising, per 100% of its weight, a proportion of between 0.5% by weight and 10% by weight of one or more self-tanning agents.

4. A method for the cosmetic treatment of the skin, the hair, the scalp and/or the lips, comprising applying an effective amount of the composition of claim 1.

5. A method for cleaning, protecting or caring for the skin, the hair, the scalp or the lips, comprising applying an effective amount of the composition of claim 1.

6. A method for artificially tanning and/or browning human skin, comprising applying an effective amount of the composition of claim 1.

7. A cosmetic treatment process for artificially tanning and/or browning human skin, comprising at least one step of applying to said human skin the composition as defined in claim 3.

* * * * *